(12) United States Patent
Agnesi

(10) Patent No.: US 10,792,502 B2
(45) Date of Patent: Oct. 6, 2020

(54) METHOD AND SYSTEM FOR ADJUSTING A NEUROSTIMULATION THERAPY

(71) Applicant: ADVANCED NEUROMODULATION SYSTEMS, INC., Plano, TX (US)

(72) Inventor: Filippo Agnesi, Plano, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 126 days.

(21) Appl. No.: 15/806,690

(22) Filed: Nov. 8, 2017

(65) Prior Publication Data
US 2019/0134410 A1 May 9, 2019

(51) Int. Cl.
*A61N 1/36* (2006.01)
*A61N 1/372* (2006.01)
(Continued)

(52) U.S. Cl.
CPC ....... *A61N 1/37247* (2013.01); *A61N 1/0534* (2013.01); *A61N 1/0551* (2013.01); *A61N 1/36067* (2013.01); *A61N 1/36167* (2013.01); *A61N 1/0476* (2013.01); *A61N 1/0509* (2013.01); *A61N 1/0512* (2013.01); *A61N 1/0514* (2013.01); *A61N 1/0524* (2013.01); *A61N 1/0531* (2013.01); *A61N 1/0553* (2013.01); *A61N 1/362* (2013.01); *A61N 1/36062* (2017.08); *A61N 1/36125* (2013.01); *A61N 1/36132* (2013.01); *A61N 1/36135* (2013.01); *A61N 1/36171* (2013.01); *A61N 1/36175* (2013.01); *A61N 1/36178* (2013.01); *A61N 1/36185* (2013.01); *G06F 19/3481* (2013.01)

(58) Field of Classification Search
CPC .............. A61N 1/37247; A61N 1/0534; A61N 1/0551; A61N 1/36067; A61N 1/3629
See application file for complete search history.

(56) References Cited

U.S. PATENT DOCUMENTS 7,212,110 B1   5/2007   Martin et al.
7,228,179 B2   6/2007   Campen et al.
(Continued)

FOREIGN PATENT DOCUMENTS

WO     20010193953 A1   12/2001

OTHER PUBLICATIONS

Int'l Search Report, dated May 2, 2019—(counterpart appl)—PCT/US2018/059832.
(Continued)

*Primary Examiner* — Joseph M Dietrich
(74) *Attorney, Agent, or Firm* — The Small Patent Law Group LLC; Dean D. Small

(57) ABSTRACT

The systems and methods described herein generally relate to adjusting a neurostimulation (NS) therapy based on drug pharmacokinetics of a patient. The systems and methods deliver an NS therapy to a portion of electrodes of a lead positioned proximate to neural tissue of interest, which is associated with a target region. The NS therapy is defined by stimulation parameters. The systems and methods determine a trigger event indicative of a drug being administered to a patient. The drug is configured to affect at least one of the neural tissue of interest or the target region. The systems and methods adjust one or more of the stimulation parameters based on the PS profile.

10 Claims, 10 Drawing Sheets

(51) Int. Cl.
*A61N 1/05* (2006.01)
*G06F 19/00* (2018.01)
*A61N 1/362* (2006.01)
*A61N 1/04* (2006.01)

(56) References Cited

U.S. PATENT DOCUMENTS

| | | |
|---|---|---|
| 7,571,007 B2 | 8/2009 | Erickson et al. |
| 2006/0170486 A1 | 8/2006 | Tranchina et al. |
| 2009/0326608 A1 | 12/2009 | Huynh et al. |
| 2011/0087307 A1 | 4/2011 | Carbunaru et al. |
| 2013/0172774 A1 | 7/2013 | Crowder et al. |
| 2014/0074179 A1 | 3/2014 | Heldman et al. |

OTHER PUBLICATIONS

Written Opinion (ISA), dated May 2, 2019—(counterpart appl)—PCT/2018/059832.
International Preliminary on Patentability for corresponding PCT Application No. PCT/US2018/059832 dated May 22, 2020.

METHOD AND SYSTEM FOR ADJUSTING A NEUROSTIMULATION THERAPY

BACKGROUND OF THE INVENTION

Embodiments herein generally relate to neurostimulation (NS) therapy and more particularly to adjusting the NS therapy based on drug pharmacokinetics of a patient.

Conventional NS systems are devices that generate electrical pulses and deliver the pulses to neural tissue to treat a variety of disorders. NS systems may be used to manage one or more conditions of a patient by delivering NS therapy. The NS systems can include deep brain stimulation, tremors, dystonia, spinal cord stimulation, dorsal root ganglion stimulation, peripheral nerve stimulation, and/or the like. The NS therapy is delivered by the NS system as electrical impulses through electrodes implanted in the one or more target regions of the nervous system. The electrical impulses are configured by a clinician based on one or more stimulation parameters (e.g., an intensity, a frequency, a pulse width, a duty cycle, an NS therapy type). The one or more stimulation parameters of the electrical impulses are static over time.

Concurrently with the static NS therapy, patients can manage the disorder using drugs. The drugs can affect the therapeutic effectiveness of the NS therapy over time. For example, the drugs can cause fluctuations of the NS therapy, such as not providing appropriate relief and/or above what is tolerable to the patient (e.g., dyskinesia in Parkinson Disease).neural tissue A need remains for improved methods and systems for adjusting NS therapy.

SUMMARY

In accordance with an embodiment, a neurostimulation (NS) system is provided. The system includes a lead having an array of electrodes positioned within a patient, and a memory having a pharmacokinetic-stimulation. In some embodiments, the PS profile provides a plurality of profile regions with each region defining a plurality of profile points that each represent a weighting factor for stimulation. The system includes a controller circuit configured to respond to instructions stored on a non-transient computer-readable medium. The controller circuit is configured to deliver an NS therapy to a portion of the electrodes proximate to neural tissue of interest that is associated with a target region. The NS therapy is defined by stimulation parameters. The controller circuit is configured to determine a trigger event indicative of a drug being administered to the patient. The drug is configured to affect at least one of the neural tissue of interest or the target region. The controller circuit is configured to adjust one or more of the stimulation parameters based for each profile point in the PS profile.

In accordance with an embodiment, a method is provided for adjusting a neurostimulation (NS) therapy. The method includes defining a PS profile for the NS therapy, wherein the PS profile provides a plurality of profile regions with each region defining a plurality of profile points that each represent a weighting factor for stimulation. The method includes delivering an NS therapy to a portion of electrodes of a lead positioned proximate to neural tissue of interest, which is associated with a target region. The NS therapy is defined by stimulation parameters. The method includes determining a trigger event indicative of a drug being administered to a patient. The drug is configured to affect at least one of the neural tissue of interest or the target region. The method includes adjusting one or more of the stimulation parameters for each profile point in the PS profile.

In accordance with an embodiment, a method is provided for adjusting a neurostimulation (NS) therapy. The method includes calculating an absorption curve of a drug over time. The absorption curve is based on a pharmacokinective characteristic of the drug. The method includes determining a response curve of a patient based on a patient profile. The patient profile represents one or more physiological characteristics of a patient. The method includes calculating a drug efficacy model based on the absorption curve and the response curve. The method includes defining a pharmacokinetic-stimulation (PS) profile based on the drug efficacy model, wherein the PS profile provides a plurality of profile regions with each region defining a plurality of profile points that each represent a weighting factor for stimulation, and transmitting the PS profile to an NS system.

DETAILED DESCRIPTION

Figure 1:
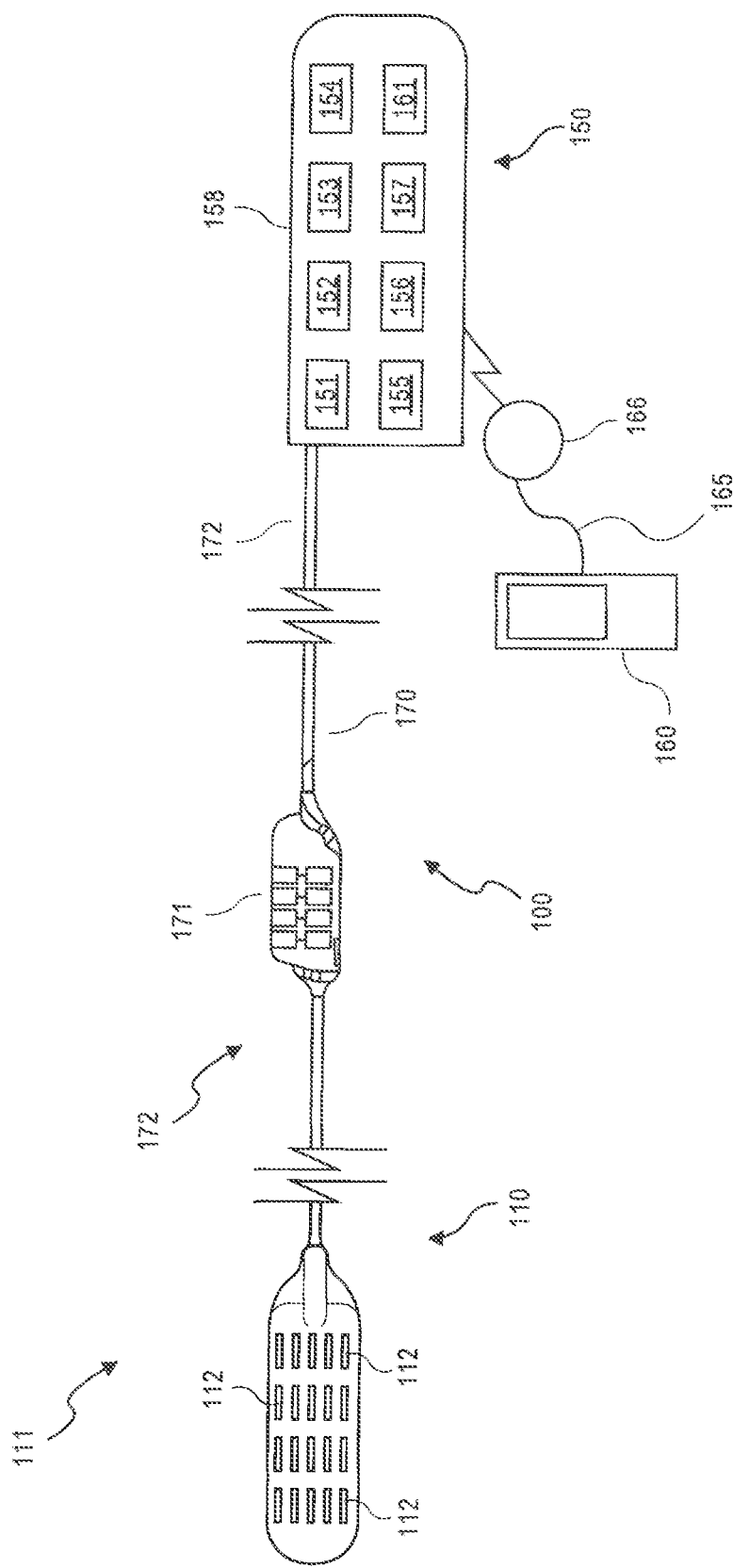
FIG. 1 depicts a schematic block diagram of an embodiment of a neurostimulation system.
Figure 2A:
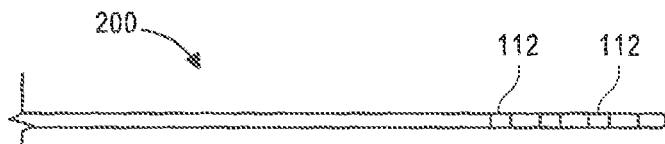
FIGS. 2A-2I respectively depict stimulation portions of embodiments for inclusion at the distal end of a lead.
Figure 2B:
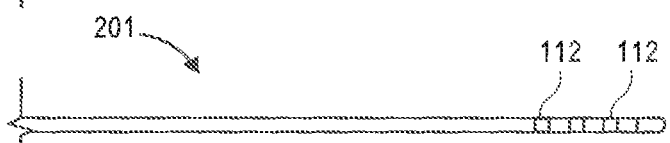
Figure 2C:
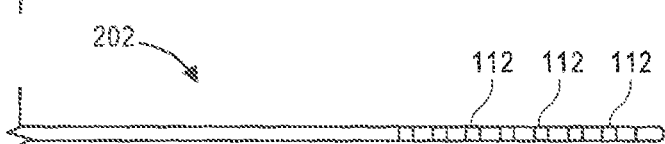
Figure 2D:
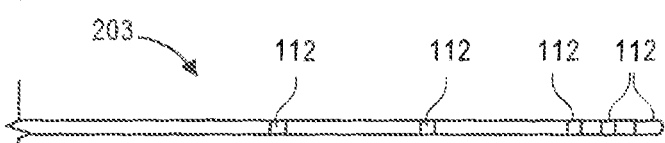
Figure 2E:
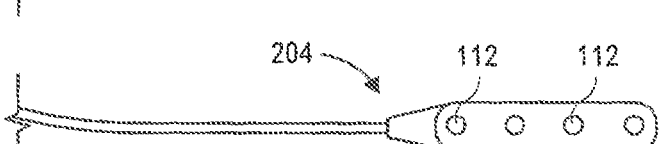
Figure 2F:
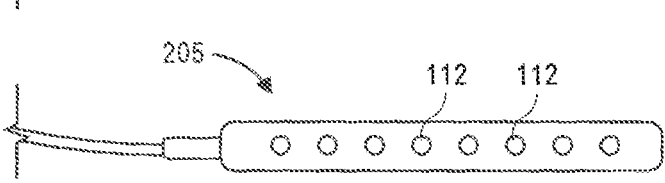
Figure 2G:
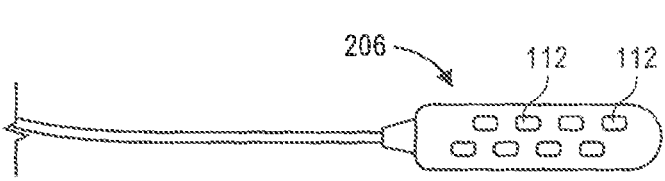
Figure 2H:
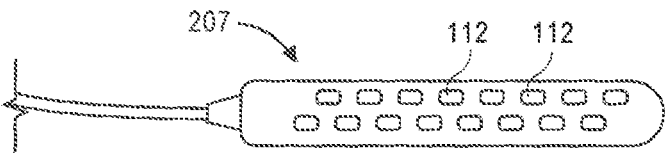
Figure 2I:
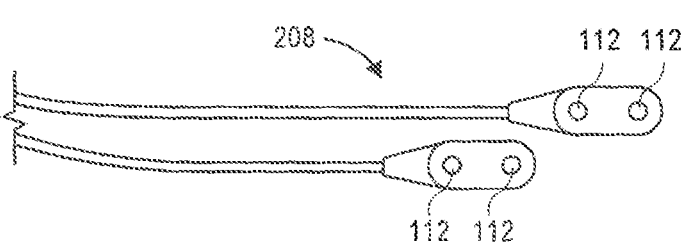

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Embodiments herein describe a neurostimulation (NS) system configured to deliver NS therapy to a target region within a patient. The NS therapy is defined by one or more stimulation parameters. The stimulation parameters define the electrical characteristics (e.g., a frequency, an amplitude, a pulse width, an amplitude, a stimulation pattern, a duty cycle, an NS therapy type) of the NS therapy. The NS therapy is delivered proximate to neural tissue of interest that is associated with a target region.

The NS system is configured to adjust the NS therapy when a trigger event is detected. The trigger event corresponds to when a drug is administered to the patient. The trigger event may be received by the NS system from an external device, such as a cell phone, laptop, computer, tablet, Near Field Communication (NFC) tag, Radio Frequency Identification (RFID) tag, drug retention device, and/or the like. Optionally, the trigger event may be based on a schedule stored in a memory of the NS system.

The NS system is configured to adjust the NS therapy (e.g., the one or more stimulation parameters) based on a pharmacokinetic-stimulation (PS) profile. The PS profile is based on a drug efficacy model. The drug efficacy model represents an effectiveness of the drug on the patient. For example, the drug efficacy model includes a range of values corresponding to the physiological effect of the drug on the patient over time. The drug efficacy model is based on an absorption curve of the drug over time, a pharmacokinetic characteristic of the drug, and a response curve of the patient.

Terms

An "absorption curve" refers to a concentration of the drug in blood plasma of the patient over time. Optionally, the absorption curve can be provided by a manufacturer of the drug, regulatory agency, and/or the like. The absorption curve may extend from when the drug is administered to the patient (e.g., the trigger event) to when the concentration of the drug is negligible and/or zero. The absorption curve is based on the chemical characteristics of the drug, a dosage of the drug, a method on how the drug is administered, and/or the like. The methods for administering the drug may include orally (e.g., capsule, pill, liquid, tablet), suppository, syringe, inhalation into the lungs, injection within the blood stream, and/or the like. The absorption curve can be derived from the pharmacokinetic characteristics of the drug. The pharmacokinetic characteristics includes a predictive model (e.g., liberation) of a rate of dissolution of the drug, a rate of movement of the drug into the bloodstream (e.g., absorption), and/or a rate of distribution of the drug in fluids and/or tissue of the patient from a site of the administration of the drug.

A "response curve" refers to a physiological response of the patient based on a concentration of the drug. The response curve is based on physiological characteristics of the patient, the dosage of the drug, the method for how the drug is administered, and/or the like. The physiological characteristics can include weight, age, height, and/or the like. The response curve includes a rate that varies based on how the concentration of the drug effects a physiology of the patient. The physiologic effect may include interruption and/or adjustment of impulses produced or received by neural tissue within the patient.

A "drug efficacy model" refers to a magnitude of physiological effects on the patient from the drug over time. The magnitude of physiological effects represents the effect of the drug on the patient. The drug efficacy model can be derived from the response curve and the absorption curve. Optionally, the drug efficacy model can be generated based on the absorption curve and a generalized response curve based on the physiological characteristics of the patient.

An "NS therapy profile" is defined by sets of stimulation parameters for the NS therapy. The NS therapy profile organizes the sets of the stimulation parameters in connection with a time period elapsed since a trigger event based on the drug efficacy model. For example, the stimulation parameters are organized such that select stimulation parameters are utilized for the NS therapy based on the magnitude of physiological effect of the drug efficacy model. Additionally or alternatively, the NS therapy profile may refer to a range of stimulation parameters and weighted factors. The weighted factors shift the stimulation parameters of the NS therapy within the range based on the drug efficacy model. For example, the NS therapy profile may have select weighted factors corresponding to the magnitude of physiological effect provided by the drug efficacy model.

A "PS profile" is defined by stimulation parameters that vary for the NS therapy in relation to a patient over time based on the trigger event. The PS profile may include the NS therapy profile and/or the drug efficacy model. Optionally, the PS profile may include temporal information representing a drug schedule of the patient.

A "trigger event" refers an event indicating that the drug is being administered to the patient. The trigger event may be communicated to the NS system from an external device. The external device can be operated by a clinician (e.g., nurse, doctor) and/or the patient. Additionally or alternatively, the trigger event may be based on the drug schedule. The drug schedule may represent points in time when the patient is administered the drug. Additionally or alternatively, the trigger event may be communicated to the NS system from a drug retention device.

"Stimulation parameters" refer to electrical characteristics of the NS therapy. The stimulation parameters may represent a pulse width, a frequency, an amplitude, a duty cycle, an NS therapy type, and/or the like. The NS therapy type can represent a characteristic of the NS therapy delivered by the NS system. The characteristic may correspond to stimulation and/or pulse patterns of the NS therapy. The pulse patterns may be a burst stimulation waveform or a tonic stimulation waveform of the NS therapy. The tonic stimulation waveform represents a pulse repeated at a rate defined by the duty cycle. The burst stimulation waveform represents a series of pulses grouped to form a pulse train. The pulse train may be repeated at a cycle rate defined by the duty cycle.

A "drug" refers to a chemical composition that is configured to interrupt and/or adjust impulses produced or received by neural tissue within the patient. For example, the drug may include levodopa, a dopamine agonist, safinamide, selegiline, rasagiline, amantadine, acetylcholinesterase inhibitor, acetaminophen, vicodin, oxycodone, ibuprofen, pethidine, dihydromorphine, codeine, cannabis, ketamine, duloxetine, and/or the like.

A "target region" refers to an area to receive treatment based on the NS therapy. For example, the target region may correspond to peripheral nerves, locations within a brain, appendages of the patient (e.g., legs, arms), one or more muscle groups, and/or the like. The target region may be proximate to and/or remote from the neural tissue of interest receiving the NS therapy. For example, the NS system can be positioned proximate to the spinal cord. The NS system delivers the NS therapy to the neural tissue of interest proximate to the spinal cord. The NS therapy is configured to provide treatment to the target region, such as the leg, arm, and/or the like distant and biologically coupled to the neural tissue of interest. Additionally or alternatively, the NS therapy is delivered to neural tissue of interest proximate to the target region. For example, the NS system may be positioned within the skull proximate to the brain. The NS system delivers the NS therapy to neural tissue of interest corresponding to the target region.

A "drug retention device" refers to a container holding one or more doses of the drug. The drug retention device may be a bottle, syringe, a drug tray, a blister package, a plastic bag, and/or the like. Optionally, the drug retention device may communicate to the NS system. For example, the drug retention device may include an RF circuit configured to communication with the NS system. For example, the RF circuit may utilize a wireless communication standard such as radio frequency identification (RFID), near field communication (NFC), Bluetooth and/or the like. The drug retention device may be configured to transmit a message indicating the trigger event to the NS system when the drug retention device is opened.

FIG. 1 depicts a schematic block diagram of an embodiment of a neurostimulation (NS) system 100. The NS system 100 is configured to generate electrical pulses (e.g., excitation pulses) for application to neural tissue of the patient according to one embodiment. For example, the NS system 100 may be adapted to stimulate spinal cord tissue, dorsal root, dorsal root ganglion (DRG), peripheral nerve tissue, deep brain tissue, cortical tissue, cardiac tissue, digestive tissue, pelvic floor tissue, and/or any other suitable neural tissue of interest within a body of a patient.

The NS system 100 includes an implantable pulse generator (IPG) 150 that is adapted to generate electrical pulses for application to tissue of a patient. The IPG 150 typically comprises a metallic housing or can 158 that encloses a controller circuit 151, pulse generating circuitry 152, a charging coil 153, a battery 154, a communication circuit 155, battery charging circuitry 156, switching circuitry 157, memory 161, and/or the like. The communication circuit 155 may represent hardware that is used to transmit and/or receive data along a uni-directional communication link and/or bi-directional communication link (e.g., with an external device 160, a drug retention device).

The controller circuit 151 is configured to control the operation of the NS system 100. The controller circuit 151 may include one or more processors, a central processing unit (CPU), one or more microprocessors, or any other electronic component capable of processing input data according to program instructions. Optionally, the controller circuit 151 may include and/or represent one or more hardware circuits or circuitry that include, are connected with, or that both include and are connected with one or more processors, controllers, and/or other hardware logic-based devices. Additionally or alternatively, the controller circuit 151 may execute instructions stored on a tangible and non-transitory computer readable medium (e.g., the memory 161).

The IPG 150 may include a separate or an attached extension component 170. The extension component 170 may be a separate component. For example, the extension component 170 may connect with a "header" portion of the IPG 150, as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within the connector portion 171 or within the IPG header for electrical connection with respective connectors. The pulses originating from the IPG 150 are provided to the one or more leads 110. The pulses are then conducted through the conductors of the lead 110 and applied to tissue of a patient via an electrode array 111. Any suitable known or later developed design may be employed for connector portion 171.

The electrode array 111 may be positioned on a paddle structure of the lead 110. For example, in a planar formation on a paddle structure as disclosed in U.S. Provisional Application No. 61/791,288, entitled, "PADDLE LEADS FOR NEUROSTIMULATION AND METHOD OF DELIVERYING THE SAME," which is expressly incorporated herein by reference. The electrode array 111 includes a plurality of electrodes 112 aligned along corresponding rows and columns. Each of the electrodes 112 are separated by non-conducting portions of the paddle structure, which electrically isolate each electrode 112 from an adjacent electrode 112. The non-conducting portions may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The electrodes 112 may be configured to emit pulses in an outward direction.

Optionally, the IPG 150 may have one or more leads 110 connected via the connector portion 171 of the extension component 170 or within the IPG header. For example, a DRG stimulator, a steerable percutaneous lead, and/or the like. Additionally or alternatively, the electrodes 112 of each lead 110 may be configured separately to emit excitation pulses.

FIGS. 2A-2I, respectively, depict stimulation portions 200-208 for inclusion at the distal end of the lead 110. For example, the stimulation portions 200-208 depict a conventional stimulation portion of a "percutaneous" lead with multiple electrodes 112. The stimulation portions 200-208 depict a stimulation portion including several segmented electrodes 112. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portions 204-208 include multiple electrodes 112 on alternative paddle structures than shown in FIG. 1.

In connection to FIG. 1, the lead 110 may include a lead body 172 of insulative material about a plurality of conductors within the material that extend from a proximal end of lead 110, proximate to the IPG 150, to its distal end. The conductors electrically couple a plurality of the electrodes 112 to a plurality of terminals (not shown) of the lead 110. The terminals are adapted to receive electrical pulses and the electrodes 112 are adapted to apply the pulses to the stimulation target of the patient. It should be noted that although the lead 110 is depicted with twenty electrodes 112, the lead 110 may include any suitable number of electrodes 112 (e.g., less than twenty, more than twenty) as well as terminals, and internal conductors.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different electrodes 112 may be generated using a single set of the pulse generating circuitry 152 using consecutively generated pulses according to a "multi-stimset program" as is known in the art. Complex stimulation parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., the tonic stimulation waveform, the burst stimulation waveform) that include generated and delivered stimulation pulses through various electrodes 112 of the one or more leads 110 as is also known in the art. Various sets of stimulation parameters may define the characteristics and timing for the pulses applied to the various electrodes 112 as is known in the art. Although constant excitation pulse generating circuitry is contemplated for some embodiments, any other suitable type of pulse generating circuitry may be employed such as constant voltage pulse generating circuitry.

Figure 3:
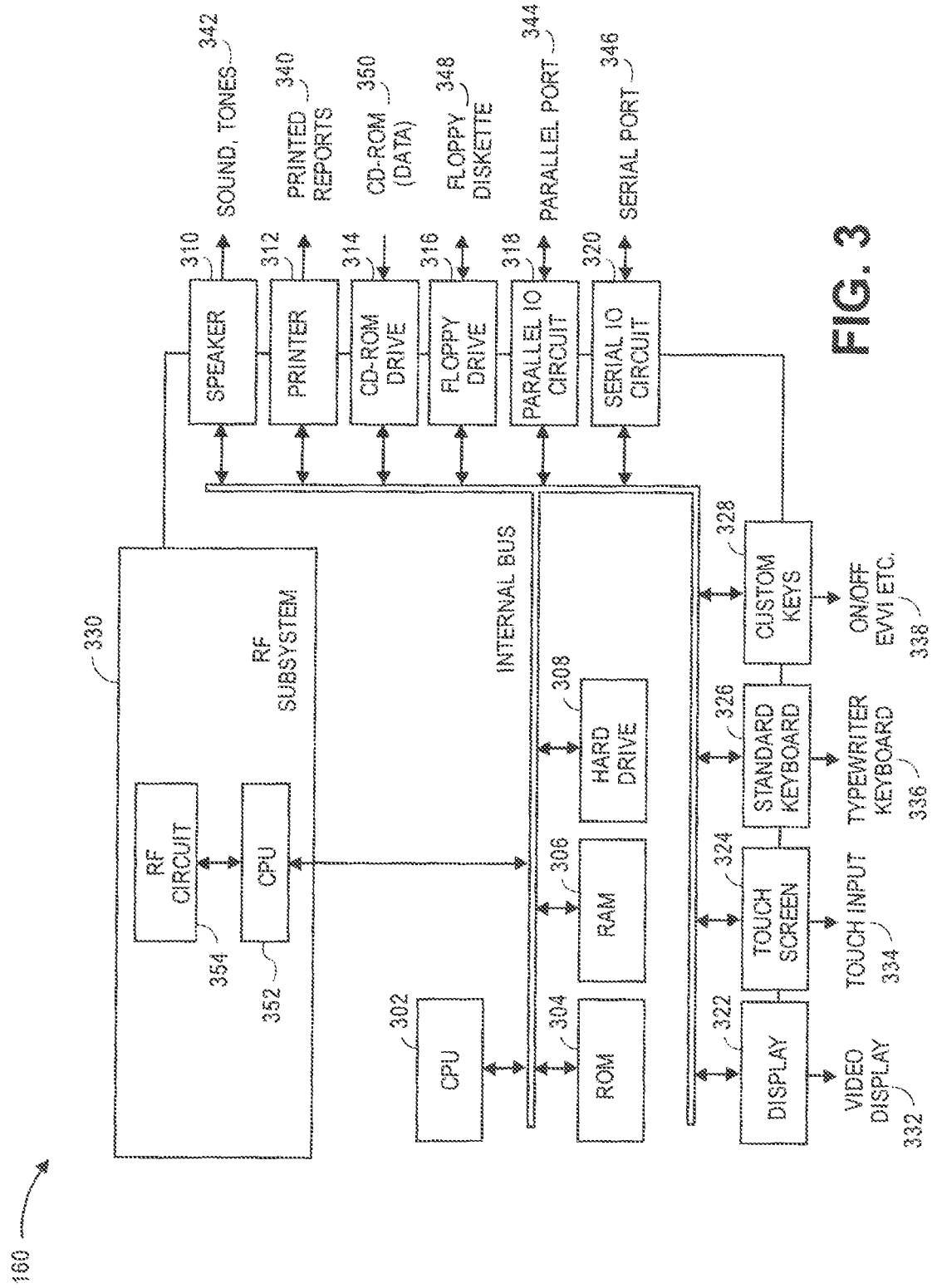
FIG. 3 illustrates a schematic block diagram of an embodiment of an external device.

The external device 160 may be implemented to charge/recharge the battery 154 of the IPG 150 (although a separate recharging device could alternatively be employed), to access the memory 161, to program the IPG 150 when implanted within the patient, to communicate triggering events to the NS system 100, and/or the like. FIG. 3 depicts a schematic block diagram of an embodiment of the external device 160. The external device 160 may be a workstation, a portable computer, an NS system programmer, a PDA, a cell phone, a smart phone, a tablet, and/or the like.

The external device 160 includes an internal bus that connects/interfaces with a Central Processing Unit (CPU) 302, ROM 304, RAM 306, a hard drive 308, a speaker 310, a printer 312, a CD-ROM drive 314, a floppy drive 316, a parallel I/O circuit 318, a serial I/O circuit 320, a display 322, a touch screen 324, a standard keyboard connection 326, custom keys 328, and a radio frequency (RF) subsystem 330. The internal bus is an address/data bus that transfers information between the various components described herein. The hard drive 308 may store operational programs as well as data, such as waveform templates and detection thresholds.

The CPU 302 is configured to control the operation of the external device 160. The CPU 302 may include one or more processors. Optionally, the CPU 302 may include one or more microprocessors, a graphics processing unit (GPU), or any other electronic component capable of processing inputted data according to specific logical instructions. Optionally, the CPU 302 may include and/or represent one or more hardware circuits or circuitry that include, are connected with, or that both include and are connected with one or more processors, controllers, and/or other hardware logic-based devices. Additionally or alternatively, the CPU 302 may execute instructions stored on a tangible and non-transitory computer readable medium (e.g., the ROM 304, the RAM 306, hard drive 308).

Optionally, the CPU 302 may include RAM or ROM memory, logic and timing circuitry, state machine circuitry, and/or I/O circuitry to interface with the NS system 100. The display 322 may be connected to a video display 332. The touch screen 324 may display graphic information relating to the NS system 100. The display 322 displays various information related to the processes described herein.

The touch screen 324 accepts a user's touch input 334 when selections are made. The keyboard 326 (e.g., a typewriter keyboard 336) allows the user to enter data to the displayed fields, as well as interface with the RF subsystem 330. The touch screen 324 and/or the keyboard 326 is configured to allow the user to operate the NS system 100. The external device 160 may be controlled by the user (e.g., doctor, clinician, patient) through the touch screen 324 and/or the keyboard 326 allowing the user to interact with the NS system 100. The touch screen 324 and/or the keyboard 326 may permit the user to move electrical stimulation along and/or across one or more of the lead(s) 110 using different electrode 112 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the touch screen 324 and/or the keyboard 326 may permit the user to designate which electrodes 112 are to stimulate (e.g., emit excitation pulses, in an anode state, in a cathode state) the stimulation target.

Custom keys 328 turn on/off 338 the external device 160. The printer 312 prints copies of reports 340 for a physician to review or to be placed in a patient file, and the speaker 310 provides an audible warning (e.g., sounds and tones 342) to the clinician and/or patient. The parallel I/O circuit 318 interfaces with a parallel port 344. The serial I/O circuit 320 interfaces with a serial port 346. The floppy drive 316 accepts diskettes 348. Optionally, the floppy drive 316 may include a USB port or other interface capable of communicating with a USB device such as a memory stick. The CD-ROM drive 314 accepts CD ROMs 350.

The RF subsystem 330 includes a central processing unit (CPU) 352 in electrical communication with an RF circuit 354. The RF subsystem 330 is configured to receive and/or transmit information with the NS system 100. The RF subsystem 330 may represent hardware that is used to transmit and/or receive data along a uni-directional and/or bi-directional communication link. The RF subsystem 330 may include a transceiver, receiver, transceiver and/or the like and associated circuitry (e.g., antennas) for wirelessly communicating (e.g., transmitting and/or receiving) with the NS system 100. For example, protocol firmware for transmitting and/or receiving data along the uni-directional and/or bi-directional communication link may be stored in the memory (e.g., the ROM 304, the RAM 306, the hard drive 308), which is accessed by the CPU 352. The protocol firmware provides the network protocol syntax for the CPU 352 to assemble data packets, establish and/or partition data received along the uni-directional and/or bi-directional communication links, and/or the like. The uni-directional and/or bi-directional communication link can represent a wireless communication (e.g., utilizing radio frequency (RF)) link for exchanging data (e.g., data packets) between the NS system 100 and the external device 160. The uni-directional and/or bi-directional communication link may be based on a customized communication protocol and/or a standard communication protocol, such as Bluetooth, NFC, RFID, GSM, infrared wireless LANs, HIPERLAN, 3G, LTE, and/or the like.

Additionally or alternatively, the RF subsystem 330 may be operably coupled to a "wand" 165 (FIG. 1). The wand 165 may be electrically connected to a telemetry component 166 (e.g., inductor coil, RF transceiver) at the distal end of wand 165 through respective wires (not shown) allowing bi-directional communication with the NS system 100. For example, the user may initiate communication with the NS system 100 by placing the wand 165 proximate to the NS system 100. Preferably, the placement of the wand 165 allows the telemetry system of the wand 165 to be aligned with the communication circuit 155.

Also, the external device 160 may permit operation of the IPG 150 according to one or more NS programs or therapies to treat the patient. For example, the NS program corresponds to the NS therapy and/or executed by the IPG 150. Each NS program may include one or more sets of stimulation parameters of the pulses including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc. The IPG 150 may modify its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 4:
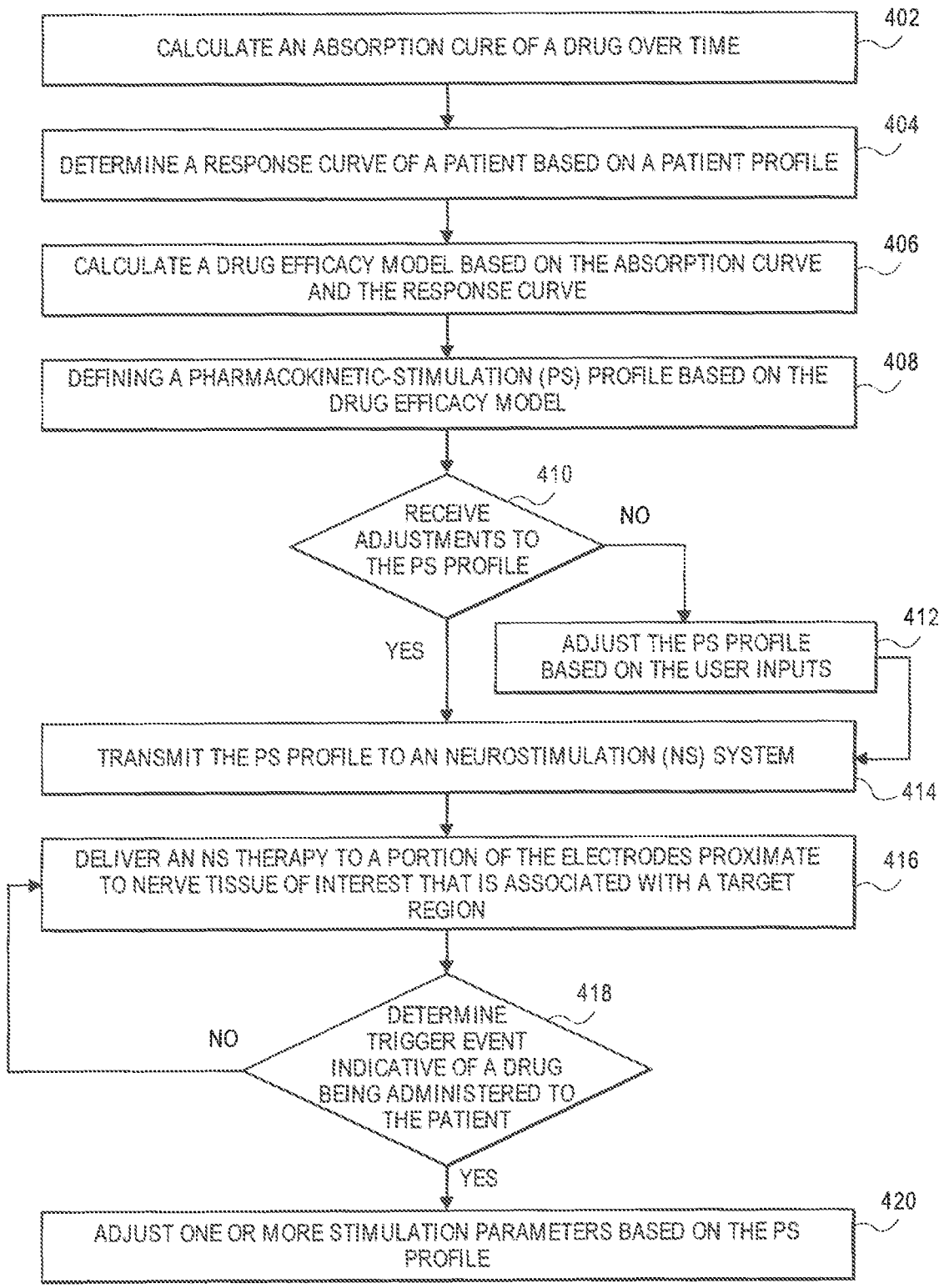
FIG. 4 illustrates a flowchart of an embodiment of a method for adjusting a neurostimulation therapy.

FIG. 4 illustrates a flowchart of an embodiment of a method 400 for adjusting a NS therapy. The method 400, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be used as one or more algorithms to direct hardware to perform one or more operations described herein.

Figure 5:
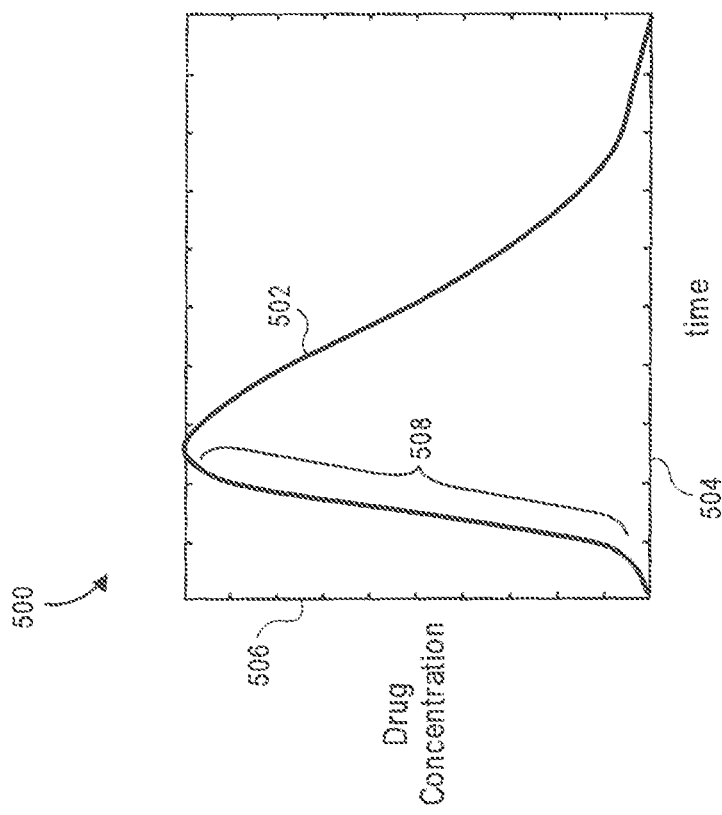
FIG. 5 illustrates a graphical representation of an embodiment of an absorption curve.

Beginning at 402, the CPU 302 calculates an absorption curve 502 of a drug over time. FIG. 5 illustrates a graphical representation 500 of an embodiment of the absorption curve 502. The absorption curve 502 is a representation of a concentration of the drug in blood plasma, shown along a vertical axis 506, of the patient over time, shown along a horizontal axis 504. The absorption curve 502 is based on a pharmacokinetic characteristics of the drug. The pharmacokinetic characteristics defines a model of a rate of concentration in the blood plasma over time. The model is based on a rate of dissolution (e.g., liberation) of the drug in the patient, a rate of movement of the drug in the bloodstream (e.g., absorption), and a rate of distribution of the drug in the fluids and/or tissue of the patient from a location of administration of the drug. The pharmacokinetic characteristics may be stored in the memory (e.g., ROM 304, RAM 306, hard drive 308) of the external device 160. Additionally or alternatively, the pharmacokinetic characteristics may be received by the external device 160 along a uni-directional and/or bi-directional communication link established by the RF subsystem 330. For example, the external device 160 may receive the pharmacokinetic characteristics from a remote server provided by a manufacturer of the drug, regulatory agency, hospital, clinic, and/or the like.

The pharmacokinetic characteristics can be different based on how the patient receives the drug (e.g., how the drug is administered, a dosage of the drug). Based on the delivery method, the CPU 302 may select a portion of the pharmacokinetic characteristics and/or adjust the pharmacokinetic characteristics. The CPU 302 can determine how the patient receives the drug based on selections by the clinician. For example, the clinician may use the touch screen 324 and/or the keyboard 326 to enter details for the method of how the patient receives the drug and/or dosage. Based on the selections by the clinician, the CPU 302 may select and/or adjust the absorption curve 502. For example, if the drug is administered by a syringe, an initial slope 508 of the absorption curve 502 may be shifted earlier in time and/or increased from the example in FIG. 5.

Figure 6:
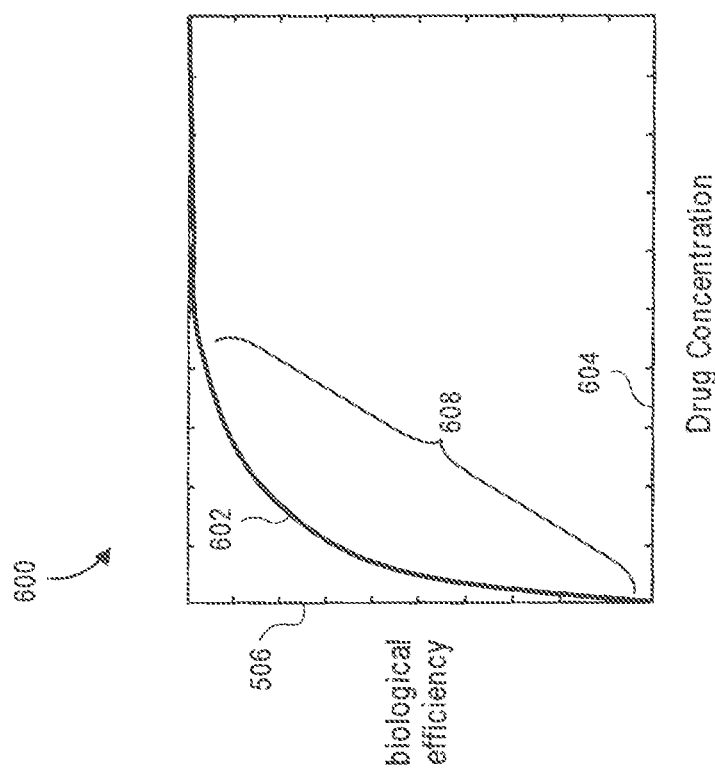
FIG. 6 illustrates a graphical representation of an embodiment of a response curve.

At 404, the CPU 302 determines a response curve 602 of a patient based on a patient profile. FIG. 6 illustrates a graphical representation 600 of an embodiment of the response curve 602. The response curve 602 is a representation of a physiological response of the patient, shown along a vertical axis 606, based on a concentration of the drug, shown along a horizontal axis 604. The physiological response of the patient is associated with changes to one or more physiological characteristics of the patient. For example, the physiological response may include an interruption and/or adjustment to the impulses produced or received by neural tissue within the patient.

The response curve 602 is affected by the patient profile. For example, the patient profile adjusts a response slope 608 of the response curve 602. The patient profile includes physiological characteristics of the patient. The physiological characteristics include a weight, an age, a height, and/or the like of the patient. The physiological characteristics affect how the drug is absorbed by the patient, a metabolism of the drug by the patient, and/or the like.

The patient profile may be stored in the memory (e.g., ROM 304, RAM 306, hard drive 308) of the external device 160. Additionally or alternatively, the patient profile may be defined by the clinician. For example, the CPU 302 may receive the patient profile based on selections by the clinician received from the touch screen 324 and/or keyboard 326. Optionally, the patient profile may be received along a uni-directional and/or bi-directional communication link from a remote server managed by a hospital, a clinic, and/or the like.

Figure 7:
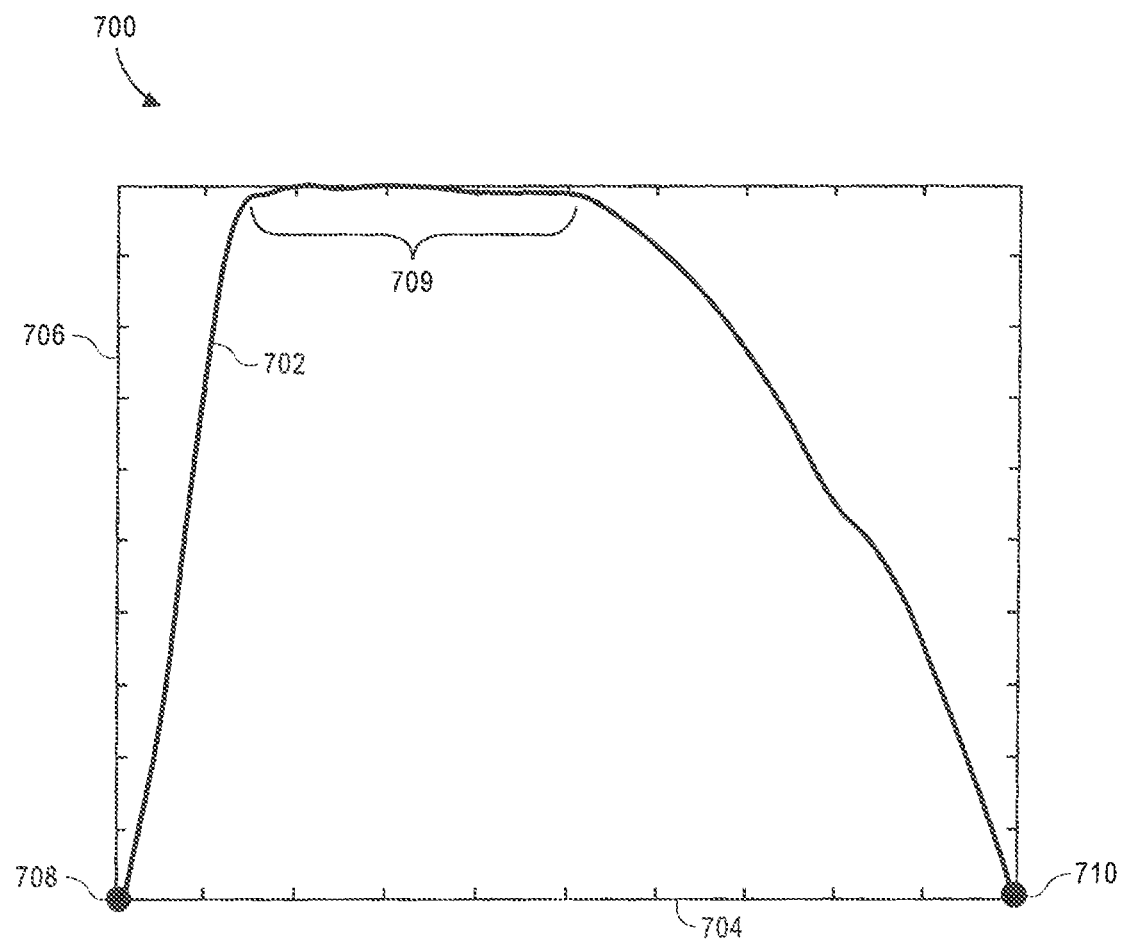
FIG. 7 illustrates a graphical representation of an embodiment of a drug efficacy model.

At 406, the CPU 302 calculates a drug efficacy model 700 based on the absorption curve 502 and the response curve 602. FIG. 7 illustrates a graphical representation of an embodiment of the drug efficacy model 700. The drug efficacy model 700 is shown as a waveform 702. The waveform 702 represents a magnitude of physiological effects of the drug on the patient, shown along a vertical axis 706, over time, shown along a horizontal axis 704. The drug efficacy model 700 is derived by the CPU 302 from the absorption curve 502 and the response curve 602. For example, the CPU 302 calculates the drug efficacy model 700 based on a convolution between the absorption curve 502 and the response curve 602. The waveform 702 includes a drug efficacy that begins at a point 708, representing the trigger event. The waveform 702 includes a peak 709. The peak 709 represents a point or range in time when the physiological effects of the drug on the patient is at a peak and/or maximum physiological effect. Over time, the waveform 702 is reduced overtime, based on a reduction in concentration of the drug until reaching a minimal point 710. The minimal point 710 represents when the point at which the physiological effects of the drug on the patient is negligible and/or not present within the patient.

At 408, the CPU 302 defines a PS profile based on the drug efficacy model 700. Optionally, the PS profile includes the drug efficacy model 700 that is based on the absorption curve 502 of the drug over time, a pharmacokinetic characteristic of the drug, and/or the response curve 602 of the patient. Additionally or alternatively, the PS profile includes an NS therapy profile over time in which a stimulation intensity is reduced as the drug efficacy increases. The PS profile includes values for the stimulation parameters of the NS therapy over time based on the trigger event (e.g., at the point 708). The PS profile may adjust the stimulation parameters of the NS therapy in connection with changes in a magnitude of the physiological effect of the drug. The adjustment to the stimulation parameters over time represent the NS therapy profile.

FIGS. 8-11 illustrate graphical representations of embodiments of PS profiles 800, 900, 1000, 1100. The PS profiles 800, 900, 1000, 1100 extend from corresponding trigger event until, through peak drug effectiveness, to a point the physiological effects of the drug are negligible and/or no longer present in the patient. The PS profiles 800, 900, 1000, 1100 are shown temporally aligned with the drug efficacy model 700. For example, the PS profiles 800, 900, 1000, 1100 are aligned with the trigger event at the point 708 of the waveform 702. The PS profiles 800, 900, 1000, 1100 include sets of stimulation parameters or weighting factors over time for the NS therapy. The sets of stimulation parameters or weighted factors that change over time. The PS profiles 800, 900, 1000, 1100 are configured to reduce a stimulation intensity of the NS therapy as the drug efficacy increases, and increases the stimulation intensity as the drug efficacy decreases. For example, the PS profiles 800, 900, 1000, 1100 are configured to have minimum stimulation parameters at the peak 709 of the waveform 702 and maximum stimulation parameters at the valleys of the drug efficacy model 700.

Figure 8:
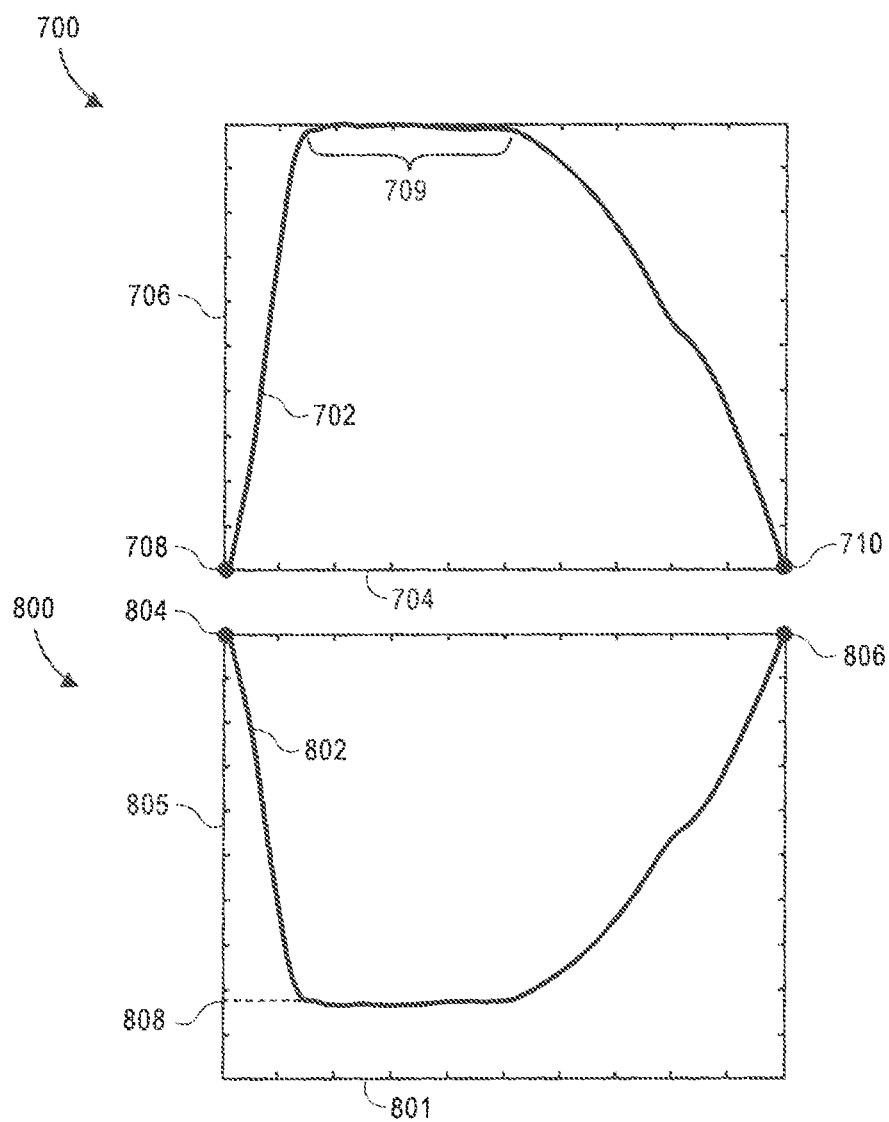
FIGS. 8-11 illustrate graphical representations of embodiments of a pharmacokinetic-stimulation profile and the drug efficacy model shown in FIG. 7.

FIG. 8 illustrates an NS therapy waveform 802 that represents the NS therapy profile for the NS therapy. The NS therapy waveform 802 extends along a horizontal axis 801 representing time, and a vertical axis 805 representing a weighted factor. The NS therapy waveform 802 extends from a maximum stimulation parameters 804 to a minimum stimulation parameters 808 and returning to a maximum stimulation parameters 806. The maximum stimulation parameters 804, 806 may correspond to the stimulation parameters for the NS therapy when the drug is not administered to the patient. For example, the maximum stimulation parameters 804, 806 are associated when the physiological effects of the drug are negligible and/or not present within the patient. The minimum stimulation parameter 808 may correspond to when the physiological effects of the drug are at the peak 709. The maximum and minimum stimulation parameters 804, 806, 808 can be stored in the memory (e.g., the ROM 304, the RAM 306, the hard drive 308). Optionally, the maximum and minimum stimulation parameters 804, 806, 808 may be defined by the clinician. For example, the CPU 302 may receive the maximum and minimum stimulation parameters 804, 806, 808 from the touch screen 324 and/or keyboard 326.

The NS therapy waveform 802 may represent weighted factors that vary over time defining the NS therapy profile. The NS therapy waveform 802 is defined as a range of stimulation parameters from the maximum stimulation parameters 804, 806 and the minimum stimulation parameter 808. The weighted factors of the NS therapy waveform 802 shift the values for the stimulation parameters along the range based on an elapsed time. For example, the weighted factors may represent a percentage and/or portion of the maximum stimulation parameters 804, 806. The portion of the maximum stimulation parameters 804, 806 may be for one or more of the stimulation parameters of the NS therapy. For example, the weighted factors may be for at least one of the pulse width, the frequency, the amplitude, the duty cycle, and/or the like of the NS therapy. The different weighted factors can represent different stimulation intensities of the stimulation parameters.

Additionally or alternatively, the weighted factors may adjust the NS therapy type. For example, the maximum stimulation parameters 804, 806 may correspond to the burst stimulation waveform. The weighted factors may represent a number of pulses of the burst stimulation waveform. The weighted factors continually reduce a number of pulses grouped to form the pulse train of the burst stimulation waveform reaching the minimum stimulation parameter 808. For example, the minimum stimulation parameter 808 may represent a tonic stimulation waveform having a single pulse.

The NS therapy waveform 802 may be defined by the CPU 302 based on the drug efficacy model 700. For example, the NS therapy waveform 802 may represent an inverse of the waveform 702. The CPU 302 may normalize the inverse of the waveform 702 to form the NS therapy waveform 802. For example, the CPU 302 may adjust opposing ends and minimum of the inverse of the NS therapy waveform 802 to match the maximum and minimum stimulation parameters 804, 806, 808.

Figure 9:
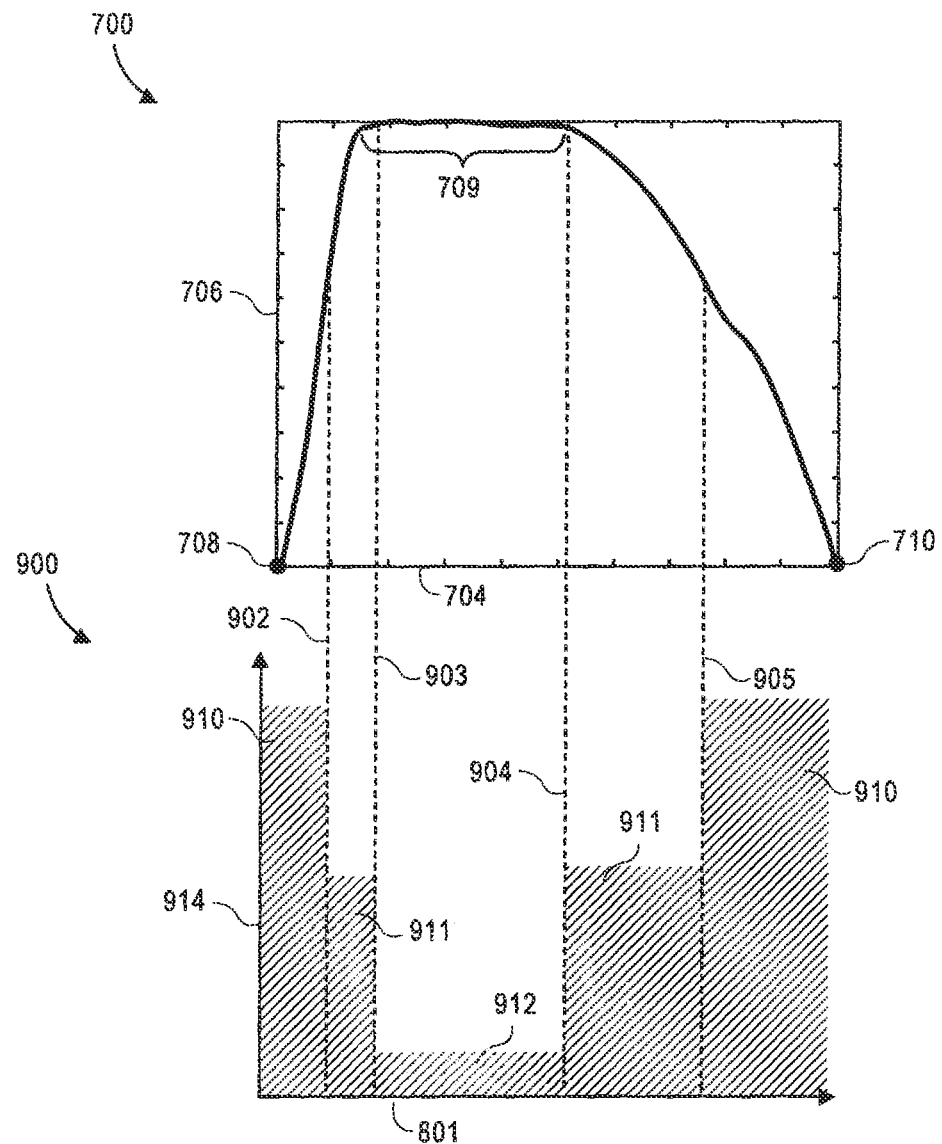

FIG. 9 illustrates a set of stimulation parameters 910-912 that represents the NS therapy profile of different stimulation parameters of the NS therapy. For example, the set of stimulation parameters 910-912 can have at least one different stimulation parameter such as the pulse width, the frequency, the amplitude, the duty cycle, the NS therapy type, and/or the like with respect to each other. The set of stimulation parameters 910-912 may correspond to different stimulation intensities of the NS therapy, which are plotted along a vertical axis 914. The vertical axis 914 representing the stimulation intensity. For example, the set of stimulation parameters 910 have a larger stimulation intensity than the set of stimulation parameters 911-912. In another example, the set of stimulation parameters 911 have a larger stimulation intensity than the set of stimulation parameters 912. The difference in the stimulation intensity can be based on a magnitude of the pulse width, the frequency, the amplitude, the duty cycle, and/or the like relative to the remaining sets of stimulation parameters 910-912.

The set of stimulation parameters 910-912 occur over a duration of time. The duration of the set of stimulation parameters 910-912 is based on the drug efficacy model 700. For example, the duration of the set of stimulation parameters 910-912 may be based on the magnitude of physiological effects (e.g., along the vertical axis 706) shown from the drug efficacy model 700. The magnitude of physiological effects may define thresholds 902-905. The magnitudes may correspond to different threshold 902-905. The thresholds 902-905 may define the duration of the set of stimulation parameters 910-912. For example, from the trigger event to the patient to the threshold 902 may define the duration of the set of stimulation parameters 910. The set of stimulation parameters 910 may correspond to a maximum stimulation parameter. For example, the set of stimulation parameters 910 may be similar to and/or the same as the maximum stimulation parameters 804, 806.

Between the thresholds 902 and 903 and the thresholds 904 and 905, define the duration for the set of stimulation parameters 911. The thresholds 903 and 904 define the duration for the set of stimulation parameters 912. The set of stimulation parameters 912 represent a minimum stimulation parameters of the PS profile 900. The set of stimulation parameters 912 is configured by the CPU 302 to occur during the peak 709 of the drug efficacy model 700. The set of stimulation parameters 912 may correspond to a minimum stimulation parameters. For example, the set of stimulation parameters 912 may be similar to and/or the same as the minimum stimulation parameters 808. The threshold 905 to the minimal point at 710 may define the set of stimulation parameters 910.

Additionally or alternatively, the PS profile may include more than three set of stimulation parameters 910-912 and/or less than three set of stimulation parameters.

Figure 10:
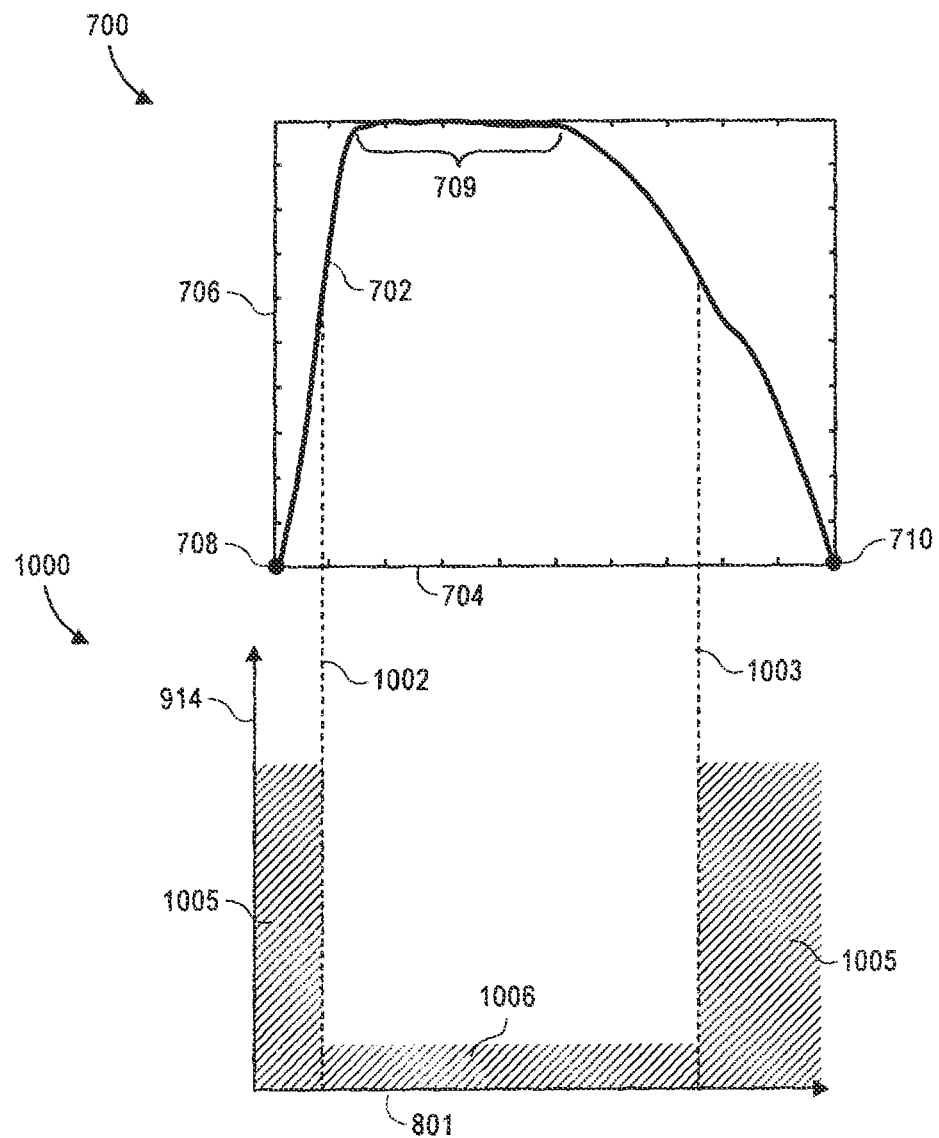

FIG. 10 illustrates a set of stimulation parameters 1005-1006 that represents the NS therapy profile for the NS therapy. The set of stimulation parameters 1005-1006 may represent different stimulation parameters of the NS therapy. For example, the set of stimulation parameters 1005-1006 can have at least one different stimulation parameter such as the pulse width, the frequency, the amplitude, the duty cycle, the NS therapy type, and/or the like with respect to each other. The set of stimulation parameters 1005-1006 may correspond to different stimulation intensities of the NS therapy. The set of stimulation parameters 1005 may correspond to a maximum stimulation parameter. For example, the set of stimulation parameters 1005 may be similar to and/or the same as the maximum stimulation parameters 804, 806. The set of stimulation parameters 1006 may correspond to a minimum stimulation parameters. For example, the set of stimulation parameters 1006 may be similar to and/or the same as the minimum stimulation parameters 808.

The set of stimulation parameters 1005-1006 occur over a duration and vary over time. Similar to and/or the same as the set of stimulation parameters 910-912, the set of stimulation parameters 1005-1006 is based on the drug efficacy model 700. For example, the duration of the set of stimulation parameters 1005-1006 may be based on the magnitude of physiological effects defining thresholds 1002-1003. The thresholds 1002-1003 may define the duration of the set of stimulation parameters 1005-1006. For example, when the drug is administered to the patient to the threshold 1002 may define the duration of the set of stimulation parameters 1005. Between the thresholds 1002 and 1003, define the duration for the set of stimulation parameters 1006. The set of stimulation parameters 1006 having lower stimulation intensity relative to the set of stimulation parameters 1005 is configured to occur during the peak 709. The threshold 1006 to the minimal point at 710 may define the set of stimulation parameters 1005.

The sets of stimulation parameters 910-912, 1005-1006 can be stored in the memory (e.g., the ROM 304, the RAM 306, the hard drive 308). Optionally, sets of stimulation parameters 910-912, 1005-1006 may be defined by the clinician. For example, the CPU 302 may receive the sets of stimulation parameters 910-912, 1005-1006 from the touch screen 324 and/or keyboard 326.

Figure 11:
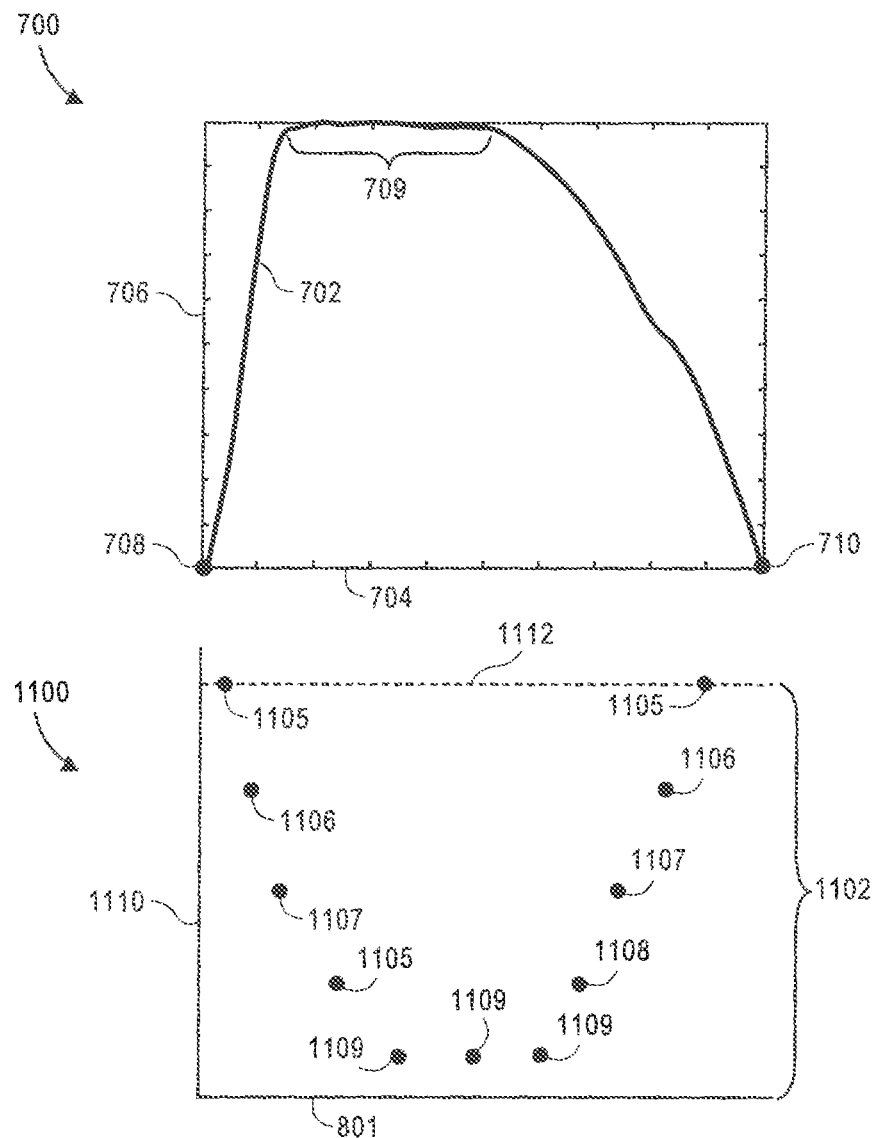

FIG. 11 illustrates weighted factors 1105-1109 that represents the NS therapy profile for the NS therapy. The weighted factors 1105-1109 shift values of the stimulation parameters of the NS therapy along a range 1102 based on an elapsed time. The weighted factors 1105-1109 correspond to different stimulation intensities plotted along a vertical axis 1110. The weighted factors 1105-1109 are positioned at different points within the range 1102 and in time. The positions of the weighted factors 1105-1009 are based on the magnitude of the physiological effect of the drug efficacy model 700. For example, the weighted factors 1105-1109 are configured such that a minimum stimulation intensity occurs during the peak 709. The weighted factors 1105-1109 adjust at least one different stimulation parameter, such as the pulse width, the frequency, the amplitude, the duty cycle, the NS therapy type, and/or the like of the NS therapy relative to a maximum stimulation parameters 1112. For example, the weighted factors 1105-1109 may represent a percentage of a maximum stimulation parameters 1112. The weighted factors 1105-1109 may correspond to a reduction of the maximum stimulation parameters 1112. For example, the weighted factors 1105-1109 may be associated with a portion of the maximum stimulation parameters 1112.

At 410, the CPU 302 determines whether adjustments are received to the PS profile 800, 900, 1000, 1100. For example, the CPU 302 may determine based on selections by the clinician from the touchscreen 324 or the keyboard 326 to adjust the PS profile 800, 900, 1000, 1100.

If the CPU 302 determined that adjustments were received, then at 412, the CPU 302 adjusts the PS profile 800, 900, 1000, 1100 based on the received clinician inputs. Optionally, the adjustments to the PS profile 800, 900, 1000, 1100 adjust the stimulation intensity of the NS therapy profile. For example, the clinician may administer the drug to the patient. The clinician may adjust the maximum stimulation parameters 804, 806, 1112, the sets of stimulation parameters 910-912, 1005-1006, and/or the weight factors 1105-1109 based on patient feedback. If the patient feels pain from the NS therapy after the drug is administered, the clinician may reduce the maximum stimulation parameters 804, 806, 1112, the sets of stimulation parameters 910, 1005, and/or the weight factors 1105. If the patient feels pain during the peak 709 of the drug efficacy model 700, the clinician may decrease the minimum stimulation parameters 808, the sets of stimulation parameters 912, 1006, and/or the weight factors 1109.

At 414, the external device 160 transmits the PS profile 800, 900, 1000, 1100 to the NS system 100. For example, the CPU 302 instructs the RF subsystem 330 to transmit the PS profile 800, 900, 1000, 1100 along a uni-directional and/or bi-directional communication link. Additionally or alternatively, the CPU 302 may instruct the RF subsystem 330 to transmit the PS profile 800, 900, 1000, 1100 based on selections by the clinician. For example, the clinician may instruct the CPU 302 to transmit the PS profile 800, 900, 1000, 1100 based on a selection from the touch screen 324 and/or the keyboard 326. When the PS profile 800, 900, 1000, 1100 is received by the NS system 100, the controller circuit 151 (FIG. 1) stores the PS profile 800, 900, 1000, 1100 in the memory 161.

At 416, the controller circuit 151 instructs the IPG 150 to deliver the NS therapy to a portion of the electrodes 112 proximate to neural tissue of interest that is associated with the target region. The portion of the electrodes 112 may be selected when the NS system 100 is implanted within the patient. For example, the portion of the electrodes 112 from the electrode array 111 can be selected by the clinician when programmed by the external device 160. The portion of the electrodes 112 are selected by the clinician to deliver the NS therapy to the neural tissue of interest.

At 418, the controller circuit 151 determines if the trigger event is received. The trigger event is indicative of the drug being administered to the patient. The trigger event can be received from the external device 160. For example, the external device 160 may be managed by the clinician and/or the patient. When the drug is being administered to the patient (e.g., orally, syringe, suppository), the CPU 302 receives a selection from the clinician and/or the patient from the touch screen 324 and/or keyboard 326 to represent the trigger event. Based on the selection, the CPU 302 instructs the RF subsystem 330 to transmit the trigger event along the uni-directional and/or bi-directional communication link to the NS system 100.

Additionally or alternatively, the trigger event may be based on a drug schedule stored in the memory 161. For example, the PS profile 800, 900, 1000, 1100 may include temporal information representing the drug schedule. The temporal information may represent times during the day, week, month, year, and/or the like when the drug is administered to the patient. The controller circuit 151 may compare the temporal information to a system clock. When the temporal information matches the system clock, the controller circuit 151 determines that the trigger event is received.

Additionally or alternatively, the trigger event is received by the controller circuit 151 from the drug retention device. The drug retention device is configured to house one or more doses of the drug. The opening of the drug retention device is indicative of the patient being administered the drug. The drug retention device can include an RF circuit. The RF circuit may be configured to transmit the trigger event to the NS system 100 when the drug retention device is opened. The trigger event can be communicated to the NS system 100 via a uni-directional and/or bi-directional communication link. When the trigger event is received by the NS system 100, the controller circuit 151 determines that the trigger event is received.

At 420, the controller circuit 151 instructs the IPG 150 to adjust the one or more of the stimulation parameters based on the PS profile 800, 900, 1000, 1100. The adjustment of the one or more of the stimulation parameters is based on the trigger event. For example, the trigger event representing a start of the PS profile 800, 900, 1000, 1100.

In connection with FIG. 8, the controller circuit 151 instructs the IPG 150 to adjust the one or more of the stimulation parameters corresponding to the weighting factors of the PS profile 800. For example, the controller circuit 151 may traverse along the NS therapy waveform 802 representing the NS therapy profile. The NS therapy waveform 802 defining weighting factors to shift values of the one or more of the stimulation parameters along the range. The range defined between the maximum stimulation parameter 804, 806 and the minimum stimulation parameter 808 of the NS therapy waveform 802. The controller circuit 151 applies the weighting factors to shift the one or more of the stimulation parameters. For example, the controller circuit 151 adjusts the one or more of the stimulation parameters based on the weighting factors with respect to the maximum stimulation parameters 804, 806 over time relative to the trigger event.

In connection with FIG. 9, the controller circuit 151 instructs the IPG 150 to adjust the one or more of the stimulation parameters corresponding to the weighting factors of the PS profile 900. For example, the controller circuit 151 adjusts the one or more of the stimulation parameters correspond to the sets of the stimulation parameters 910-912. The controller circuit 151 adjusts the one or more of the stimulation parameters to the set of the stimulation parameters 910-912 based on durations defined by the thresholds 902-905. For example, the controller circuit 151 adjusts the one or more of the stimulation parameters from the set of the stimulation parameters 910 to the set of the stimulation parameters 911 after the duration defined by the threshold 902.

In connection with FIG. 11, the controller circuit 151 instructs the IPG 150 to adjust the one or more of the stimulation parameters corresponding to the weighting factors of the PS profile 1100. For example, the controller circuit 151 adjusts the one or more of the stimulation parameters correspond to the sets of the weighted factors 1105-1109 representing the NS therapy profile. The controller circuit 151 applies the weighted factors 1105-1109 to shift values of the one or more stimulation parameters along the range 1102. For example, the controller circuit 151 adjusts the one or more of the stimulation parameters based on the weighted factors 1105-1109 over time relative to the trigger event.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A neurostimulation (NS) system, comprising:
a lead having an array of electrodes positioned within a patient;
a memory having a pharmacokinetic-stimulation (PS) profile, wherein the PS profile provides a plurality of profile regions with each region defining a plurality of profile points that each represent a weighting factor for stimulation; and
a controller circuit configured to respond to instructions stored on a non-transient computer-readable medium, to:
deliver a NS therapy to a portion of the electrodes proximate to neural tissue of interest that is associated with a target region, wherein the NS therapy is defined by stimulation parameters;
determine a trigger event indicative of a drug being administered to the patient, the drug configured to affect at least one of the neural tissue of interest or the target region; and
adjust one or more of the stimulation parameters for each profile point in the PS profile, wherein the controller circuit adjusts the one or more of the stimulation parameters by scaling a pulse amplitude for each respective generated pulses according to a corresponding profile point in the plurality of profile points for the respective regions of the plurality of profile regions.

2. The system of claim 1, wherein the PS profile includes a drug efficacy model that is based on an absorption curve of the drug over time, a pharmacokinetic characteristic of the drug, and a response curve of a patient.

3. The system of claim 1, wherein the PS profile includes an NS therapy profile over time in which a stimulation intensity is reduced as a drug efficacy increases.

4. The system of claim 3, wherein the NS therapy profile reduces the one or more stimulation parameters over time to reduce the stimulation intensity.

5. The system of claim 3, wherein the NS therapy profile includes first and second sets of the stimulation parameters, wherein the controller circuit to select between the first and second sets of the stimulation parameters based on an elapsed time relative to the trigger event.

6. The system of claim 5, further comprising a communication circuit configured to communicate with an external device and to receive the first and second sets of the stimulation parameters from the external device.

7. The system of claim 3, wherein the NS therapy profile includes a range for the stimulation parameters, wherein the controller circuit to apply a weighting factor to shift values for the stimulation parameters along the range based on an elapsed time relative to the trigger event.

8. The system of claim 1, further comprising a communication circuit configured to receive the trigger event from an external device.

9. A method for adjusting a neurostimulation (NS) therapy, comprising:
calculating an absorption curve of a drug over time, wherein the absorption curve is based on a pharmacokinective characteristic of the drug;
determining a response curve of a patient based on a patient profile, wherein the patient profile represents one or more physiological characteristics of a patient;
calculating a drug efficacy model based on the absorption curve and the response curve;
defining a pharmacokinetic-stimulation (PS) profile based on the drug efficacy model, wherein the PS profile provides a plurality of profile regions with each region defining a plurality of profile points that each represent a weighting factor for stimulation; and
transmitting the PS profile to an NS system.

10. The method of claim 9, wherein the PS profile includes an NS therapy profile over time having a range of stimulation parameters for an NS therapy, further comprising defining a weighting factor to shift values for the stimulation parameters along the range based on a morphology of the drug efficacy model.

* * * * *